United States Patent
Lechmann et al.

(10) Patent No.: US 8,940,052 B2
(45) Date of Patent: Jan. 27, 2015

(54) EXPANDABLE IMPLANT

(71) Applicant: DePuy Synthes Products, LLC, Raynham, MA (US)

(72) Inventors: Beat Lechmann, Oberdorf (CH); Dominique Burkard, Gretzenbach (CH); Michael Schwager, Winterthur (CH)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 13/784,955

(22) Filed: Mar. 5, 2013

(65) Prior Publication Data

US 2014/0031938 A1     Jan. 30, 2014

Related U.S. Application Data

(60) Provisional application No. 61/675,975, filed on Jul. 26, 2012.

(51) Int. Cl.
    *A61F 2/44*          (2006.01)
    *A61F 2/46*          (2006.01)
    *A61F 2/30*          (2006.01)

(52) U.S. Cl.
CPC .............. *A61F 2/442* (2013.01); *A61F 2/441* (2013.01); *A61F 2/447* (2013.01); *A61F 2/4611* (2013.01); *A61F 2002/30179* (2013.01); *A61F 2002/30467* (2013.01); *A61F 2002/30537* (2013.01); *A61F 2002/3055* (2013.01); *A61F 2002/30556* (2013.01); *A61F 2002/30579* (2013.01); *A61F 2002/30583* (2013.01);
(Continued)

(58) Field of Classification Search
USPC ............. 606/246–249, 279; 623/17.11–17.16
See application file for complete search history.

(56) References Cited

U.S. PATENT DOCUMENTS

| 5,772,661 | A | 6/1998 | Michelson |
| 5,860,973 | A | 1/1999 | Michelson |

(Continued)

FOREIGN PATENT DOCUMENTS

| DE | 202008001079 | 3/2008 |
| WO | WO 2005/112834 | 12/2005 |

(Continued)

OTHER PUBLICATIONS

International Patent Application No. PCT/US2013/029014: International Search Report dated Jul. 1, 2013, 7 pages.

(Continued)

*Primary Examiner* — Mary Hoffman
*Assistant Examiner* — Christina Negrellirodrigue
(74) *Attorney, Agent, or Firm* — Baker & Hostetler LLP (57) ABSTRACT

An expandable implant for inserting within a skeletal space is provided, and a method for using the implant to expand the skeletal space. The implant is preferably designed to be inserted into an intervertebral space to replace at least part of an intervertebral disc between adjacent vertebral bodies. The expandable implant contains at least one first expansion compartment and at least one second expansion compartments, which compartments can be inflatable balloons that are inflated by a catheter. Inflating the first expansion compartment expands the implant in a first direction and inflating the second expansion compartment expands the implant in a second direction.

22 Claims, 8 Drawing Sheets

(52) U.S. Cl.
CPC .......... *A61F 2002/30586* (2013.01); *A61F 2002/30828* (2013.01); *A61F 2002/30836* (2013.01); *A61F 2002/30909* (2013.01); *A61F 2002/30912* (2013.01); *A61F 2310/00017* (2013.01); *A61F 2310/00023* (2013.01); *A61F 2310/00029* (2013.01); *A61F 2310/00047* (2013.01); *A61F 2310/00101* (2013.01); *A61F 2310/00359* (2013.01); *A61F 2310/00407* (2013.01); *A61F 2310/00796* (2013.01)
USPC .............. 623/17.16; 623/17.11; 606/246

(56) References Cited

U.S. PATENT DOCUMENTS

| | | | |
|---|---|---|---|
| 6,102,950 | A | 8/2000 | Vaccaro |
| 6,193,757 | B1 | 2/2001 | Foley et al. |
| 6,723,126 | B1 | 4/2004 | Berry |
| 6,953,477 | B2 | 10/2005 | Berry |
| 6,969,404 | B2 | 11/2005 | Ferree |
| 6,969,405 | B2 | 11/2005 | Suddaby |
| 7,083,650 | B2 | 8/2006 | Moskowitz et al. |
| 7,887,589 | B2 | 2/2011 | Glenn et al. |
| 7,951,199 | B2 | 5/2011 | Miller |
| 7,993,403 | B2 | 8/2011 | Foley et al. |
| 8,021,424 | B2 | 9/2011 | Beger et al. |
| 8,043,381 | B2 * | 10/2011 | Hestad et al. .............. 623/17.16 |
| 2002/0151976 | A1 | 10/2002 | Foley et al. |
| 2007/0118222 | A1 | 5/2007 | Lang |
| 2007/0198089 | A1 | 8/2007 | Moskowitz et al. |
| 2007/0233244 | A1 | 10/2007 | Lopez et al. |
| 2008/0243251 | A1 | 10/2008 | Stad et al. |
| 2009/0054991 | A1 | 2/2009 | Biyani |
| 2009/0222096 | A1 * | 9/2009 | Trieu .......... 623/17.16 |
| 2009/0222099 | A1 * | 9/2009 | Liu et al. .......... 623/17.16 |
| 2009/0248159 | A1 * | 10/2009 | Aflatoon .......... 623/17.12 |
| 2010/0262240 | A1 * | 10/2010 | Chavatte et al. .......... 623/17.11 |
| 2010/0286783 | A1 | 11/2010 | Lechmann et al. |
| 2011/0301711 | A1 | 12/2011 | Palmatier et al. |

FOREIGN PATENT DOCUMENTS

| | | |
|---|---|---|
| WO | WO 2006/058281 | 6/2006 |
| WO | WO 2009/092102 | 7/2009 |
| WO | WO 2014/018098 | 1/2014 |

OTHER PUBLICATIONS

U.S. Appl. No. 61/675,975, filed Jul. 26, 2012, Lachmann et al.

* cited by examiner

EXPANDABLE IMPLANT

CROSS REFERENCE TO RELATED APPLICATIONS

This application claims the benefit of U.S. Provisional Patent Application Ser. No. 61/675,975 filed Jul. 26, 2012, the contents of which are hereby incorporated by reference herein in their entirety. All documents cited herein are incorporated by reference in their entirety.

TECHNICAL FIELD

This invention relates to improved implants for a skeletal space. This invention also relates to improved methods for expanding a skeletal space and for treating a patient having skeletal damage or injury.

BACKGROUND

There are many situations where there is a need to replace, augment or support sections of bone in human or animal bodies, such as for replacement of material between or within bones in the spine, long bones in the arms or legs, in the knee, hip, shoulder, finger or other joints and following removal of a portion of bone due to tumour treatment or injury. In particular, there is a requirement for support or realignment of neighbouring vertebrae for treating damage to the spine, for example due to osteoporosis or damage to a vertebral disc. Expandable intervertebral implants which can be inserted into a patient's spine at a relatively small size and which are able to expand to restore the original height of removed spinal material or to a height desired by a surgeon in order to support and/or realign the spine are known from WO 2009/092102.

WO 2009/092102 discloses implants that may be sequentially expanded in an intervertebral space using a surgical instrument to perform lateral expansion in the anterior-posterior (a-p) direction and then using a balloon to expand the implant in the cranio-caudal (c-c) direction. However, it has been found that when an instrument is used to expand the implant in the a-p direction, it is difficult to achieve the desired dimension of the intervertebral implant in the a-p direction (the implant "footprint"). One reason for this is the difficulty in accessing the implant with an appropriate instrument when the implant is located in a surgically sensitive site, such as between vertebrae, due to the potential risk of tissue and nerve damage to the patient. An alternative method for effecting a-p expansion of the implant disclosed in WO 2009/092102 is using the pre-installed balloon. However, this results in an inherent expansion of the implant in the c-c direction. A disadvantage of this arrangement is that there is a risk that the implant will contact the vertebrae too early during the c-c expansion, thereby limiting the a-p expansion achievable and, hence, preventing the degree of a-p expansion within the intervertebral space desired by the surgeon. A consequence of insufficient a-p expansion of the implant is that the implant may be less effective at supporting and/or aligning the vertebrae and may not allow sufficiently high biomechanical performance.

It is desirable to provide an expandable implant that is able to be inserted into a skeletal space in a patient at a relatively small size and which is configured to be able to expand in a controlled, sequential fashion to dimensions desired by a medical practitioner. In particular, it is desirable to be able to restrict expansion in at least one direction in which the implant is able to expand during expansion of the implant in a perpendicular direction, in order to provide more control over the dimensions of the finally expanded implant.

Furthermore, it would be desirable to provide a method of expanding a skeletal space using an expandable implant in a sequential fashion that allows the dimensions of the expanded implant to be controlled.

SUMMARY

According to the present invention, there is provided an implant for a skeletal space, comprising:
  a first contacting member;
  a second contacting member;
  at least one first expansion compartment; and
  at least one second expansion compartment;
  wherein the implant is expandable from an insertion configuration to an expanded configuration,
  wherein the implant has a first dimension in a first direction and a second dimension in a second direction in the insertion configuration, and wherein the first direction is substantially perpendicular to the second direction,
  wherein the implant is configured such that:
    during expansion of the at least one first expansion compartment, the at least one first expansion compartment cooperates with at least one of the first and second contacting members to cause the first dimension of the implant to increase without substantially causing a change in the second dimension of the implant; and
    during expansion of the at least one second expansion compartment, the at least one second expansion compartment cooperates with at least one of the first and second contacting members to cause the second dimension of the implant to increase.

As such, the implant can be expanded in the first direction to achieve the required first dimension for the implant within a skeletal space without changing the second dimension of the implant and then subsequently can be expanded in the second direction to achieve the required second dimension of the implant within the skeletal space. An advantage of the implant is that it allows expansion in at least one dimension of the implant to be restricted during expansion of the implant in another dimension. Having the ability to select the direction in which the dimension of the implant is able to expand, provides a medical practitioner with improved control over expanding the implant to the appropriate dimensions within the skeletal space.

The implant may be configured such that during expansion of the at least one second expansion compartment, the at least one second expansion compartment cooperates with at least one of the first and second contacting members to cause the second dimension of the implant to increase without substantially causing a change in the first dimension of the implant. As such, the implant can be expanded in the first direction to achieve the required first dimension for the implant within a skeletal space without changing the second dimension of the implant and then subsequently can be expanded in the second direction to achieve the required second dimension of the implant within the skeletal space without affecting the previously obtained first dimension. Alternatively, the implant may be expanded initially in the second direction with subsequent expansion in the first direction. In this way, the implant provided has an advantage of being able to be expanded in a controlled fashion so that both first and second dimensions of the implant may be optimised.

The implant may be manufactured by any appropriate means. For example, the implant may be manufactured by manufacturing each of the first and second contacting members as separate and distinct components and then coupling these together. An exemplary method for making the implants of the present invention may be based on the method described in WO 2009/092102, or any appropriate adaptation thereof known to a person skilled in the art.

The implant may be used in any appropriate skeletal space. The implant of the present invention may be used for replacement of material between or within bones, such as in the spine, long bones in the arms or legs, in the knee, hip, shoulder, finger or other joints. Alternatively, the implant of the present invention may be used for replacement of a section of bone, such as following removal of a portion of bone due to tumour treatment or injury. The skeletal space may correspond to a section of bone removed from a femur, tibia or fibula. The skeletal space may be defined by a void between a first portion and a second portion of the same bone. Alternatively, the skeletal space may be defined by a void between a first bone and a second bone. Preferably, the skeletal space is a void between a first bone and a second bone in a joint. Preferably, the skeletal space is an intervertebral space. The intervertebral space may arise from the absence of an intervertebral disc. The intervertebral space may be defined by the space between the superior surface of a first vertebra and an inferior surface of a second, adjacent vertebra.

The first direction and second direction are substantially perpendicular to each other. The first direction and second direction may be in any direction depending on the orientation of the implant. The first direction may correspond to the direction of the height, width or depth of the implant. The second direction may correspond to the direction of the height, width or depth of the implant. Preferably, the first direction corresponds to the width of the implant and the second direction corresponds to the height of the implant. In this arrangement, the extent of the expansion of the implant in the first direction may be selected according to the width of a skeletal space and the extent of the expansion of the implant in the second direction may be selected according to the distance between a first bone or first portion of bone and a second bone or second portion of bone defining the skeletal space. Where the skeletal space is an intervertebral space, the first direction may be an anterior-posterior (a-p) direction, a cranio-caudal (c-c) direction or a medial laterally (m-1) direction. Preferably, the first direction is an a-p direction and the second direction is a c-c direction.

The first and the second contacting members may be bone contacting members. The portion of bone which the first and second contacting members contact may be bare bone or may be covered in a material, such as a protective cap or a film layer to assist in engagement of the bone with the implant.

The first and the second contacting members may be substantially planar. Alternatively, they may be shaped, such as having a convex or a concave shaped in order to better align with the portion of the bone which they abut.

The first and second contacting members may have an outer surface that contacts bone which is smooth.

Alternatively, the outer surface of the first and second contacting members may have an outer surface that is undulating. The outer surface may comprise a plurality of teeth or spikes. In this way the implant may have improved stability within the skeletal space. In particular, there may be improved engagement between the implant and the bone due to friction between the bone and the plurality of teeth.

The first and second contacting members may be formed from any suitable biocompatible material including: a metal, such as cobalt-chromium-molybdenum (CCM) alloys, titanium, titanium alloys, stainless steel, aluminium; a ceramic such as zirconium oxide, silicone nitride; an allograft; an autograft; a metal-allograft composite; a polymer, such as polyaryl ether ketone (PAEK), polyether ether ketone (PEEK), polyether ketone ketone (PEKK), polyetherketone (PEK), polyetherketone ether-ketone-ketone (PEK-EKK); and polymers reinforced with a fiber, such as a carbon fiber.

The first and second contacting members may be coated in order to enhance the osteo-integration of the implant in the skeletal space. The first and second contacting members may also be coated with thin layer titanium using a physical or chemical vapour deposition process, by an anodic plasma chemical surface treatment comprising calcium and/or phosphorus in the titanium-oxide surface layer or may be sprayed with a titanium or hydroxyapatite (HA) plasma. In this way osteo-conductive properties may be enhanced.

The first and second expansion compartments may be an inflatable structure, such as a balloon, an expansion sack or an expansion bag. Preferably, the first expansion compartment is a balloon, preferably a double-walled balloon. Preferably, the second expansion compartment is a balloon, preferably a double-walled balloon. Preferably, the first and second expansion components are both balloons, preferably double-walled balloons.

The first and second expansion compartments may be manufactured from any suitable biocompatible material including, polyurethane, a polycarbonate urethane, a polycarbonate-silicone urethane copolymer, a polyamine, a polyethylene terephthalate, and a polycaprolactone.

The use of expansion compartments in the implant enables selective, sequential expansion of the implant. Furthermore, the expansion compartments allow the implant filling material to be safely retained in order to avoid the filling material spreading out of the implant and into sensitive and easily damaged body parts.

The implant may comprise a single first expansion compartment, two first expansion compartments, or more than two first expansion compartments. Preferably, the implant comprises two first expansion compartments.

The implant may comprise a single second expansion compartment, two second expansion compartments, or more than two second expansion compartments. Preferably, the implant comprises two second expansion compartments.

The first and second expansion compartments may be configured to be able to receive a filling material independently of one another. In this way, expansion of the first and second expansion compartments can occur selectively, which has an advantage of allowing improved control over the manner in which the implant expands.

Typically, the first and second expansion compartments may each be connected to separate removable catheters. Filling material may be introduced into the expansion compartment via a catheter. The first and second expansion compartments may each comprise an entry portion into which the filling material may be introduced. Once a required amount of filling material has been introduced into the expansion compartment, the catheter may be removed.

The filling material may be any suitable biocompatible material and may be rigid or elastic. The filling material may be a bone cement, a hydrogel, a polyvinyl alcohol, a sodium polyacrylate, an acrylate polymer, a methyl-methacrylate, a copolymer with an abundance of hydrophilic groups, p-vinyl pyrollidone, polyethyleneimine, a setting or curing hydrogel based copolymer such as polyethyleneimine, poly(diethylaminoethyl methacrylate), poly(ethylaminoethyl methacrylate), a thermally setting hydrogel based copolymer such as poly-N-isopropylacrylamide with polyethylene glycol, copolymers of polyethylene oxide and polyphenelylene oxide, copolymers of polyethylene glycol and polyactides, an ionic setting hydrogel such as ethylacrylate, methacrylic acid, 1,4-butanediacrylate, or a PCU, PCU-silicone copolymer, silicone or other non-resorbable pure or elastic copolymer (for example, PCU's silicone end group modified PUs, RTV curing siloxane based elastomers).

The filling material may be curable, for example, the filling material may comprise a polymer and a cross-linking agent. The final dimensions and shape of the implant after expansion may be retained by hardening or cross-linking the filling material after the filling material has been introduced into the expansion compartment. In this way, the implant may be able to provide skeletal support where previously there had been a space.

The implant may comprise a first cavity defined in a region between the first contacting member and the second contacting member in which at least one of the second expansion compartments is housed.

The implant may further comprise a second cavity defined in a region between the first contacting member and the second contacting member in which a further second expansion compartment is housed.

The first contacting member may comprise two contacting components. Where the first contacting member comprises two contacting components, the implant further comprises a first expandable connection that links the two contacting components. The two contacting components of the first contacting member are arranged such that as the first dimension of the implant increases the first expandable connection expands and the contacting components move apart.

A third cavity may be defined in a region between the two contacting components of the first contacting member in which a first expansion compartment is housed. In this way, expansion of the first expansion compartment moves apart the two contacting components of the first contacting member.

The second contacting member may comprise two contacting components. Where the second contacting member comprises two contacting components, the implant further comprises a second expandable connection that links the two contacting components. The two contacting components of the second contacting member are arranged such that as the first dimension of the implant increases the first expandable connection expands and the contacting components move apart.

A fourth cavity may be defined in a region between the two contacting components of the second contacting member in which a first expansion compartment is housed. In this way, expansion of the first expansion compartment moves apart the two contacting components of the first contacting member.

The implant may comprise a third expandable connection that links the first contacting member to the second contacting member, wherein as the second dimension of the implant increases the third expandable connection expands.

The first, second or third expandable connections may comprise any elements that allow the contacting components or contacting members to which they are linked to move apart as described hereinabove. The expandable connections may comprise, for example, a mesh or a wire netting. The wire netting may comprise a plurality of individual link members. The individual link members may have a rectangular shape. The individual link members may have a trapezoidal shape.

The first and/or second expandable connections may comprise the at least one first expansion compartment described hereinabove. A first expansion compartment may be attached to each of the two components of one or both of the first and second contacting members such that on expansion of the first expansion compartment, the two components of the first or the second contacting members are moved apart by and remain linked together by the first expansion component. The third expandable connection may comprise the at least one second expansion compartment described hereinabove. A second expansion compartment may be attached to each of the first and second contacting members such that on expansion of the second expansion compartment, the first and second contacting members are moved apart by and remain linked together by the second expansion component.

The first, second and third expandable connections may allow expansion of the implant to any suitable dimension appropriate for the skeletal space in which the implant is being used. When the skeletal space is an intervertebral space, the expandable connections typically are each able to expand from about 0.3 mm to about 12 mm.

The first, second and third expandable connections may allow the first and second contacting members to adopt a shape that enables the implant to adapt to the shape of the skeletal space.

The implant may further comprise at least one third expansion compartment,
wherein the implant has a third dimension in a third direction in the insertion configuration, and the third direction is substantially perpendicular to each of the first and second directions,
wherein the implant is configured such that expansion of the at least one third expansion compartment causes the third dimension of the implant to increase without substantially causing a change in the first or second dimensions of the implant.

At least one, preferably both, of the first and second contacting members may each comprise four contacting components. The four contacting components may be arranged in a configuration such that there are two contacting components side by side in the first direction and two contacting components side by side in the third direction. The at least one third expansion compartment may be positioned between two contacting components in the third direction. Expansion of the third expansion compartment is able to move apart the two contacting components in the third direction. Preferably, the third expansion compartment is as hereinbefore described in relation to the first and second expansion compartments.

Where the first and second directions are height and width of the implant, the third direction corresponds to the depth of the implant. Preferably, where the skeletal space is an intervertebral space, the third direction is the m-1 direction.

The implant may further comprise a first fixing for attaching the at least one first expansion compartment to the implant. The first expansion compartment may comprise an attachment portion, such as a hook portion, for cooperating with the first fixing and allowing attachment to the implant.

The implant may further comprise a second fixing for attaching the at least one second expansion compartment to the implant. The second expansion compartment may comprise an attachment portion, such as a hook portion, for cooperating with the second fixing and allowing attachment to the implant.

The first and second fixings may be arranged at an end of the implant away from the end at which the entry portion of the first and second expansion compartments is located.

The first and second fixings may be configured to allow detachment from the implant of the at least one first expansion compartment and the at least one second expansion compartment when the implant is in the expanded configuration. In this way, the position of the first or second expansion compartments may be manipulated to allow tilting of the first contacting member of the implant with respect to the second contacting member. In an embodiment where the first and/or second contacting members comprise two or more contacting components, relative movement of one or more contacting components within a plane of the first and/or second contacting members may be achieved.

Detachment of the first or second expansion compartment from the implant may also be advantageous in the event that the implant should be removed from the skeletal space. Removal of the first or second expansion compartments may allow the implant to reduce in size and adopt the insertion configuration, which would make removal from the skeletal space less damaging to the patients other body parts.

The implant may comprise a mechanism for engaging an implant holding and/or insertion instrument. The mechanism for engaging an implant holding and/or insertion instrument may comprise one or more grooves, apertures, mouldings, channels or projections arranged on the first or second contacting members. For example, the mechanism may be arranged to receive one or more pairs of blade springs of an implant holding and/or insertion instrument.

The implant may comprise one or more features, such as one or more form fit features, that assist the contacting components of the first and second contacting members to fit together prior to expansion of the first and/or second expansion compartments. These features are useful in order to help retain the implant in an insertion configuration during implantation. These features may comprise one or more grooves, apertures, mouldings, channels or projections arranged on the first or second contacting members to enable the first and second contacting members to retain their position relative to each other prior to expansion of the implant.

In accordance with the present invention, there is provided a method of expanding an implant in a skeletal space comprising:

inserting an expandable implant in a skeletal space, the implant comprising first and second expansion compartments;

expanding the first expansion compartment to expand a first dimension of the implant in a first direction; and subsequently expanding the second expansion compartment to expand a second dimension of the implant in a second direction;

wherein the first direction is different to the second direction.

The first direction may be perpendicular to the second direction.

The method may comprise a step of arranging the first and second expansion compartments in the expandable implant prior to inserting the expandable implant in a skeletal space. Alternatively, the method may comprise a step of providing an implant in which the first and second expansion compartments have been arranged in the implant prior to insertion of the implant.

The method may comprise preventing substantially any expansion of the second dimension of the implant in a second direction during the step of expanding the first expansion compartment. Alternatively or in addition, the method may comprise preventing substantially any expansion of the first dimension of the implant in a first direction during the step of expanding the second expansion compartment.

The method may further comprise evaluating the position of the implant prior to expanding the second expansion compartment. Evaluation of the position of the implant may be achieved by using standard techniques such as fluoroscopy. A fluoroscope, also known as an image intensifier, may be used to evaluate the position of the implant intraoperatively and in real time. The implant may be engaged with an implant holding and/or insertion instrument during the evaluation. This has an advantage of allowing repositioning of the implant as appropriate.

Prior to insertion of the implant, the end portions of the bone at the edge of the skeletal plates may be cleaned. Furthermore, tissue may be removed from the skeletal space prior to insertion of the implant.

The skeletal space is as hereinbefore described. Preferably, the skeletal space is an intervertebral space. Where the skeletal space is an intervertebral space, the method preferably comprises a step of removing an intervertebral disc from the intervertebral space prior to the step of inserting the implant in the intervertebral space.

The implant may be inserted in an intervertebral space via abdominal, trans-psoas or extraforaminal approaches.

The implant used in the method of the present invention may have features as in any of the implants hereinbefore described.

The implant may comprise a first contacting member and a second contacting member. Preferably, the first and the second contacting members are bone contacting members. The implant may be configured such that in the step of expanding the first expansion compartment, the first expansion compartment cooperates with at least one of the first and second contacting members to cause the first dimension of the implant to increase. Alternatively or in addition, the implant may be configured such that in the step of expanding the second expansion compartment, the second expansion compartment cooperates with at least one of the first and second contacting members to cause the second dimension of the implant to increase.

In the method of the present invention, the implant may have at least two second expansion compartments, and the method may comprise expanding one second expansion compartment more than the other second expansion compartment in order to tilt the first contacting member with respect to the second contacting member.

According to the present invention there is provided a method of treating skeletal damage in a patient comprising implanting in a skeletal space an implant of the present invention.

According to the present invention there is provided a method of treating skeletal damage in a patient comprising inserting an implant of the present invention and expanding the implant according to the method of expanding a skeletal space hereinbefore described.

DETAILED DESCRIPTION

Specific embodiments of the present invention are now described by way of example only with reference to the drawings. It will be recognised that features specified in one embodiment of the invention may be combined with other specified features to provide further embodiments.

Figure 1:
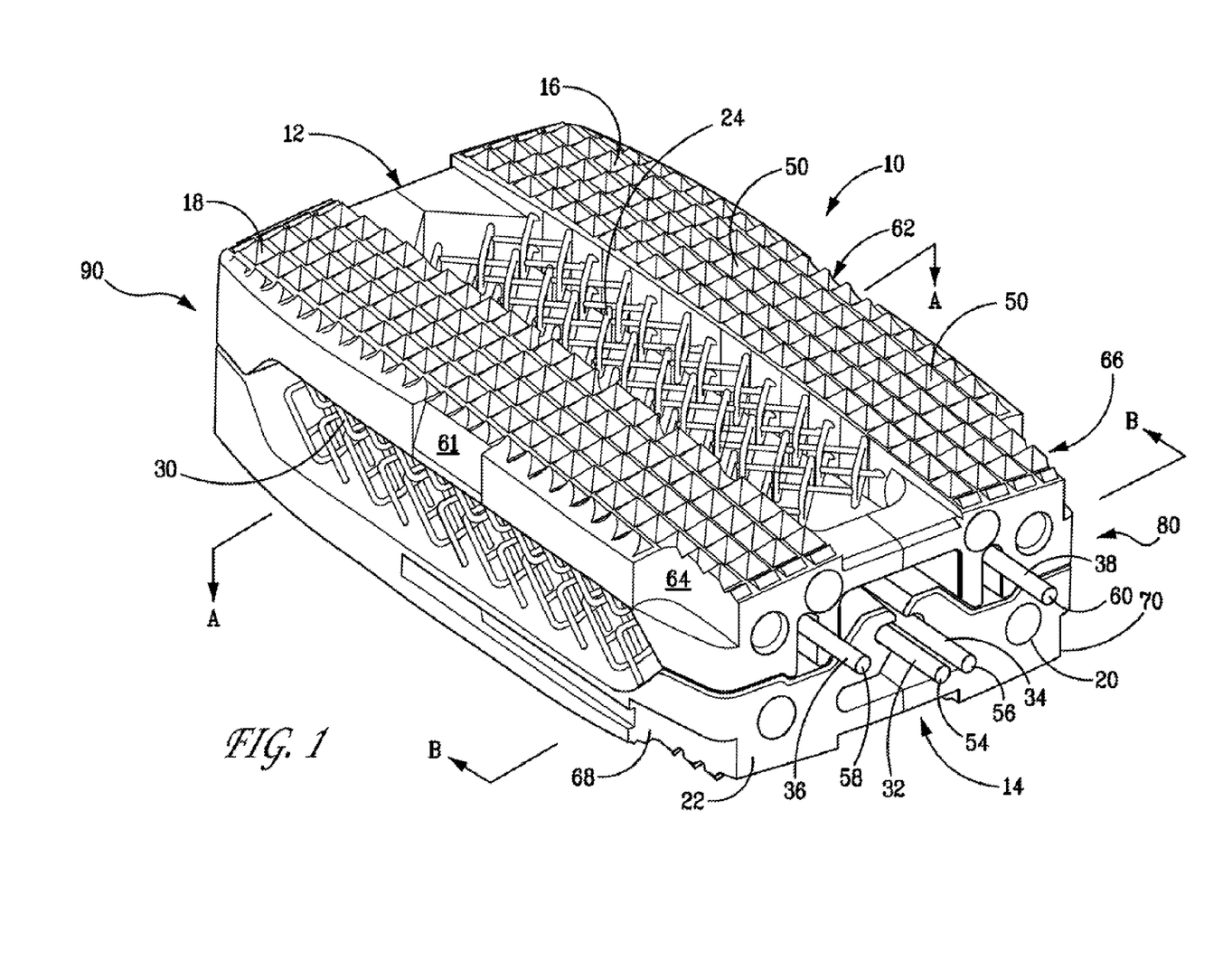
FIG. 1 is a top perspective view of an implant according to the present invention in an insertion configuration.
Figure 2:
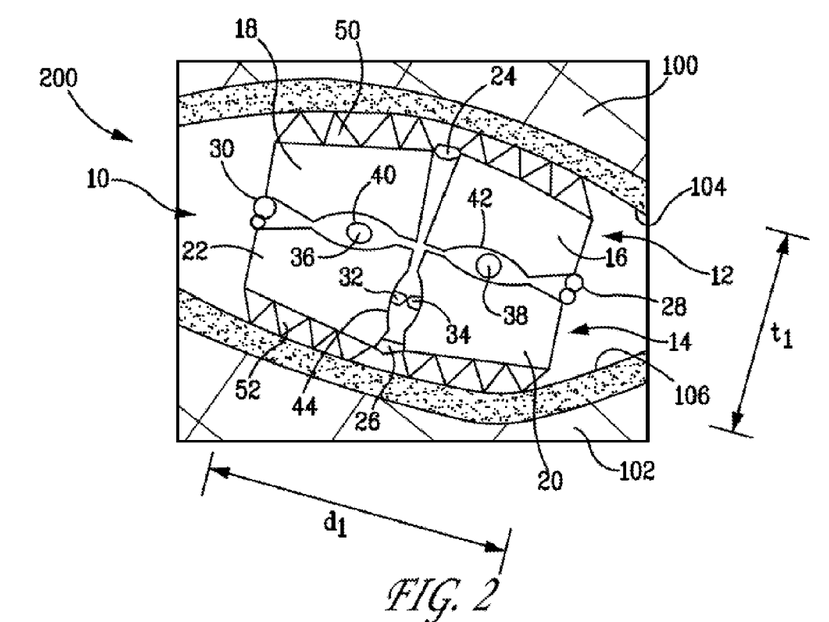
FIG. 2 is a cross-sectional view of the implant shown in FIG. 1 taken through the plane A-A.
Figure 3:
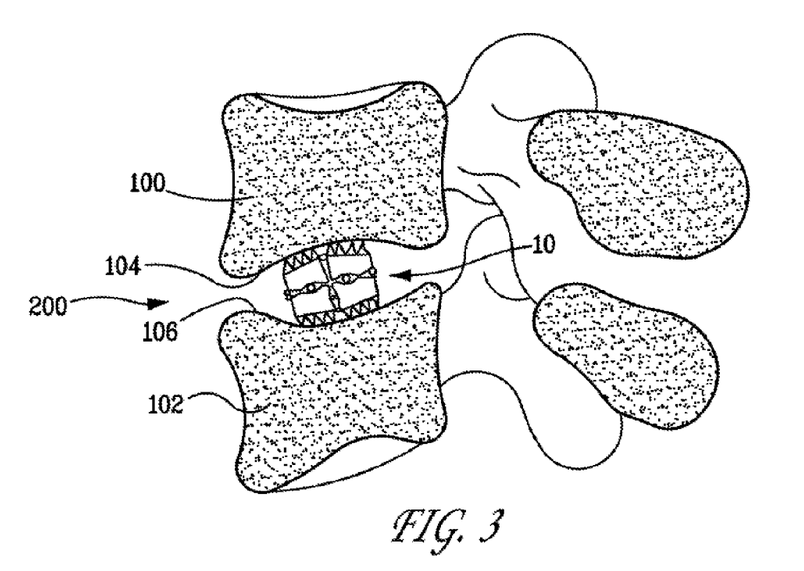
FIG. 3 is a cross-sectional view of an implant shown in FIG. 1 positioned in an intervertebral space.

With reference to FIGS. 1, 2 and 3, an implant (10) according to one embodiment of the present invention is shown in an insertion configuration. The implant has a front end (80) and a rear end (90). The implant (10) has a first contacting member (12) consisting of two contacting components (16, 18) linked by a first expandable connection (24) and a second contacting member (14) consisting of two contacting components (20, 22) linked by a second expandable connection (26). The first contacting member (12) and the second contacting member (14) are linked by a third expandable connection (28, 30).

The implant (10) has a first cavity (40) between one contacting component (18) of the first contacting member (10) and one contacting component (22) of the second contacting member (14) in which is housed a second expansion compartment (36). The implant (10) also has a second cavity (42) between the other contacting component (16) of the first contacting member (12) and the other contacting component (20) of the second contacting member (14) in which is housed a further second expansion compartment (38). The two second expansion compartments are in the form of longitudinally shaped balloons.

The implant (10) has a third cavity (44) between the contacting components (20, 22) of the second contacting member (14) in which are housed two first expansion compartments (32, 34). The first expansion compartments are in the form of longitudinally shaped balloons.

The contacting components (16, 18) of the first contacting member (12) each have a plurality of teeth (50) on their outermost surface. The contacting components (20, 22) of the second contacting member (14) each have a plurality of teeth (52) on their outermost surface.

The two first expansion compartments (32, 34) may be filled with filling material via a catheter (not shown) attached to an entry portion (54, 56) of each of the first expansion compartments.

The two second expansion compartments (36, 38) may be filled with filling material via a catheter (not shown) attached to an entry portion (58, 60) of each of the second expansion compartments.

The first contacting member (12) comprises a groove (61, 62) on the outer edge of each of the contacting components (16, 18) to which an implant holding and insertion instrument (not shown) can be attached to the implant (10).

The first contacting member (12) comprises recesses (64, 66) and the second contacting member comprises recesses (68, 70) to which an implant holding and insertion instrument (not shown) can be attached to the implant (10).

While in the insertion configuration, the implant (10) may be inserted into a skeletal space. FIGS. 2 and 3 show the implant (10) inserted into an intervertebral space (200) between a first vertebra (100) and a second vertebra (102). The implant (10) may be inserted into the intervertebral space (200) through a lateral incision in a patient. An implant holding and insertion instrument (not shown) engages with an arrangement of grooves (61, 62) and recesses (64, 66, 68, 70) on the implant (10) and the implant holding and insertion instrument is used to insert the implant into the intervertebral space (200). The implant holding and insertion instrument (not shown) is then detached from the implant (10). In the insertion configuration, the implant has a dimension $d_1$ in a first direction and a dimension $t_1$ in a second direction.

When inserted into the intervertebral space, the plurality of teeth (50) on the outermost surface of the first contacting member (12) engage with a surface (104) of the first vertebra (100) and the plurality of teeth (52) on the outermost surface of the second contacting member (14) engage with a surface (106) of the second vertebra (102).

Figure 4:
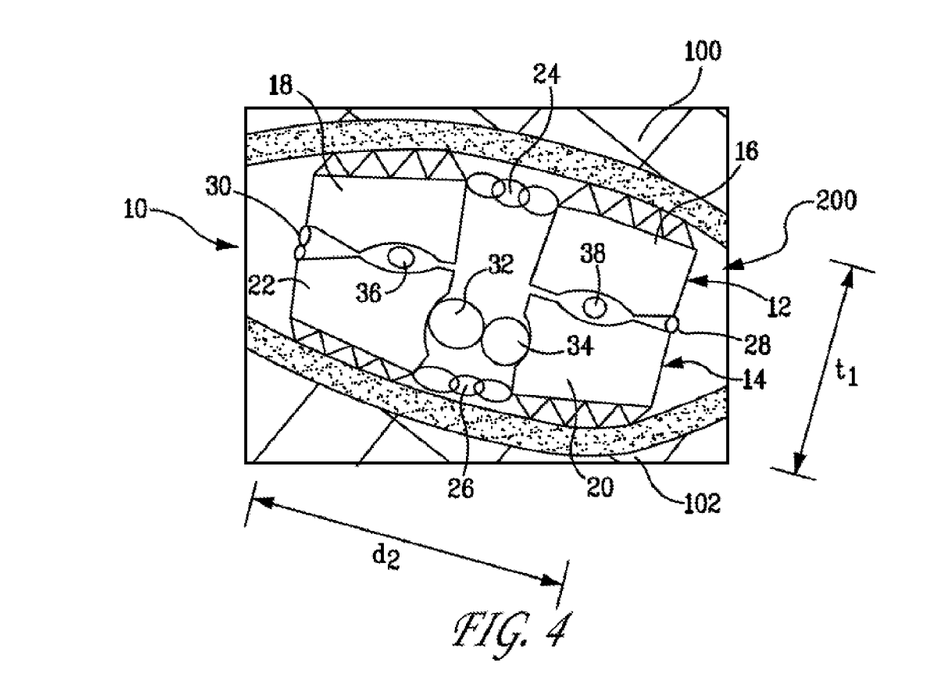
FIG. 4 is a cross-sectional view of the implant shown in FIG. 1 which has been expanded in a first direction.
Figure 5:
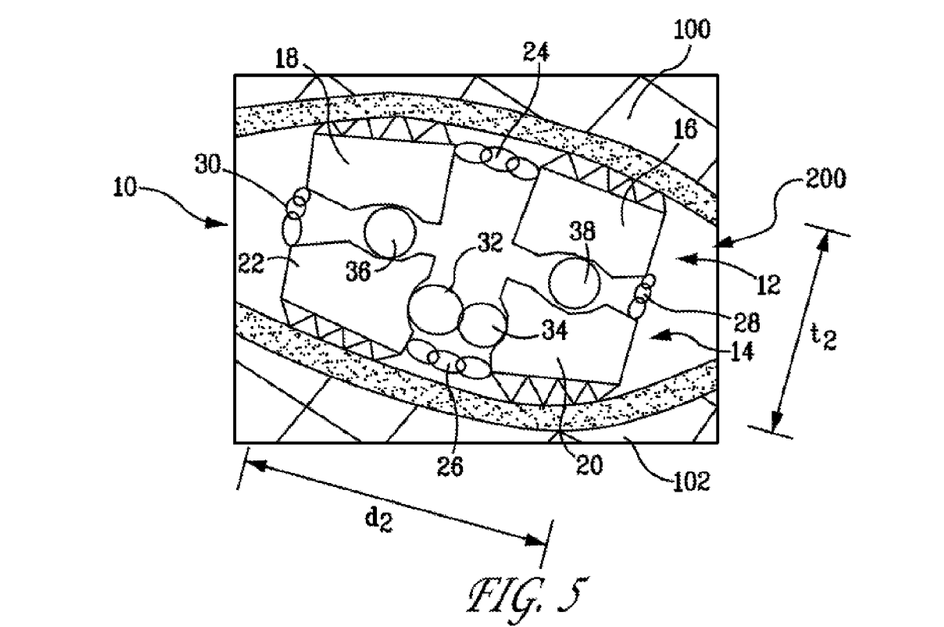
FIG. 5 is a cross-sectional view of the implant shown in FIG. 1 which has been expanded in a first direction and in a second direction.

With reference to FIGS. 4 and 5, which show features corresponding to those in FIGS. 2 and 3, the sequential expansion of the embodiment described in FIGS. 1 to 3, is effected by first simultaneously expanding the first expansion compartments (32, 34) with a filler material via catheters (not shown). Expansion of the first expansion compartments (32, 34) causes the first expandable connection (24) and the second expandable connection (26) to expand and the contacting components (16, 18) in the first contacting member (12) to move apart such that the implant has a dimension $d_2$ in the first direction. The third expandable connection (28, 30) does not expand and the dimension $t_1$ in the second direction remains unchanged. In this embodiment, the implant (10) is inserted such that the first direction corresponds to the a-p direction.

Subsequent to expansion of the first expansion compartments (32, 34), expansion in second direction, which corresponds to the c-c direction, is effected by simultaneously expanding the second expansion compartments (36, 38). Expansion of the second expansion compartments (36, 38) causes the third expandable connection (28, 30) to expand and the first and second contacting members (12, 14) to move apart such that the implant has a dimension $t_2$ in the second direction. The dimension $d_2$ in the second direction remains unchanged.

Figure 6:
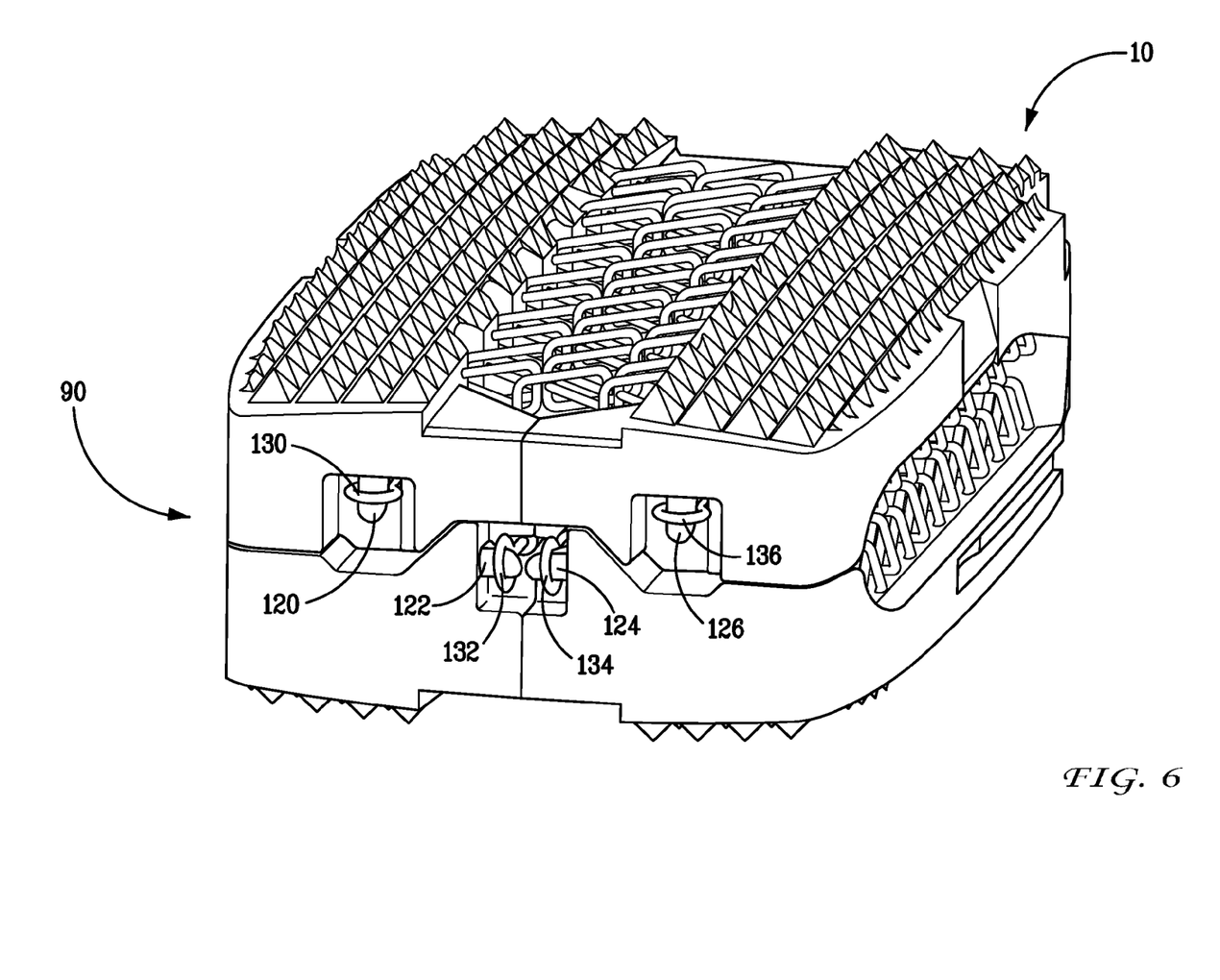
FIG. 6 is a rear perspective view of the implant shown in FIG. 1 in an insertion configuration.
Figure 7:
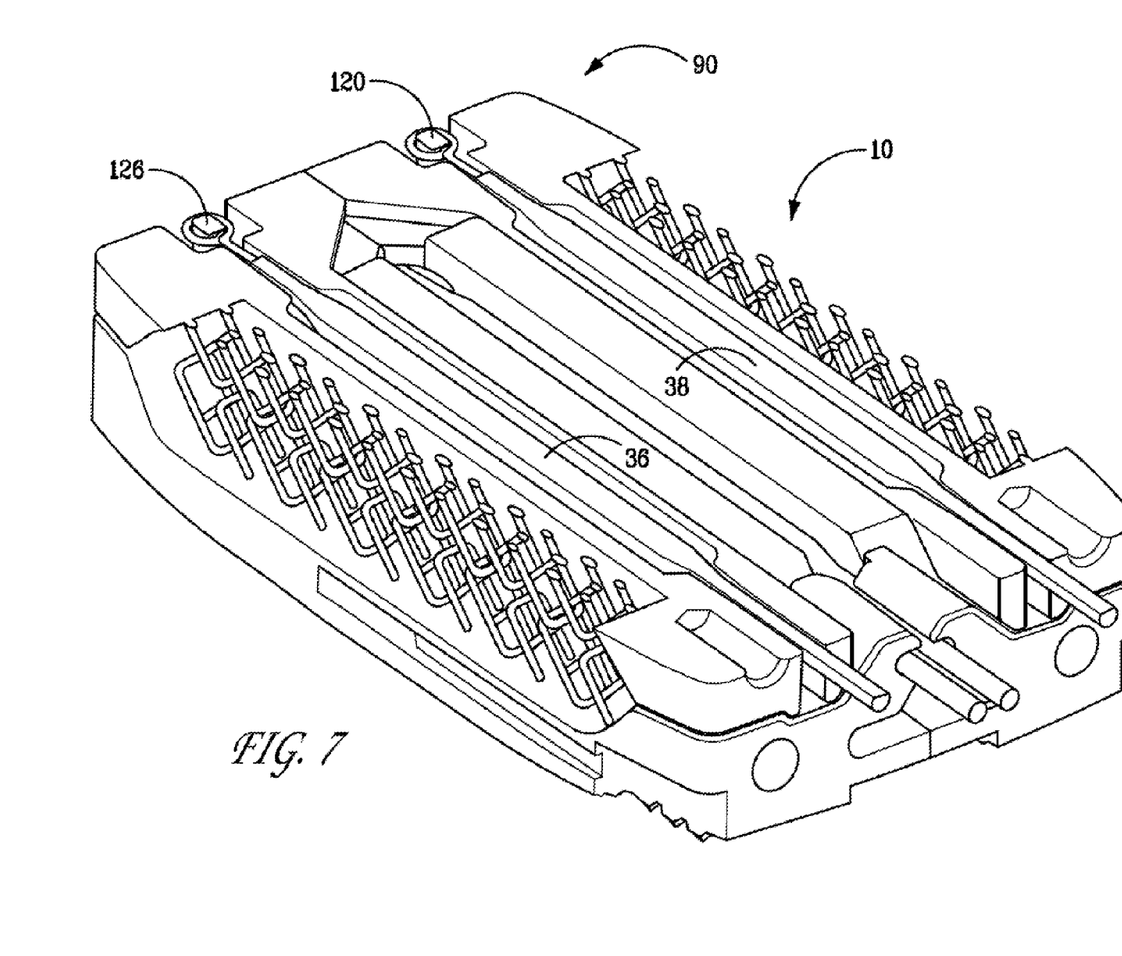
FIG. 7 is a cross-sectional view of the implant shown in FIG. 1 taken through the plane B-B.

With reference to FIGS. 6 and 7 the first expansion compartments (32, 34) each comprise a hook portion (132, 134) that cooperates with first fixings (122, 124) positioned at the rear end (90) of the implant (10) to attach the first expansion compartments (32, 34) to the implant (10). The second expansion compartments (36, 38) each comprise a hook portion (130,136) that cooperates with second fixings (120, 126) positioned at the rear end (90) of the implant (10) to attach the second expansion compartments (36, 38) to the implant (10).

Figure 8:
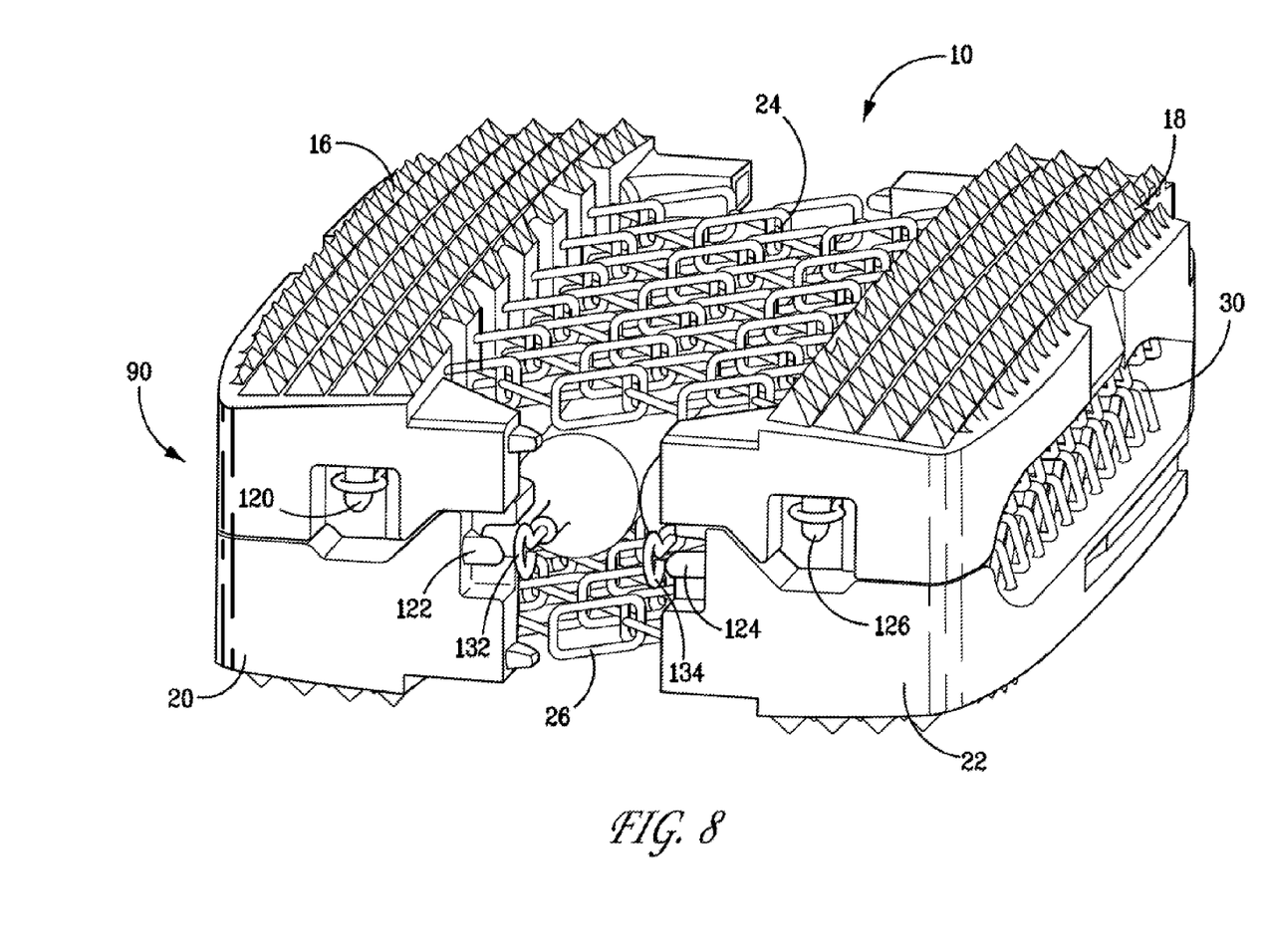
FIG. 8 is a rear perspective view of the implant shown in FIG. 1 which has been expanded in a first direction.
Figure 9:
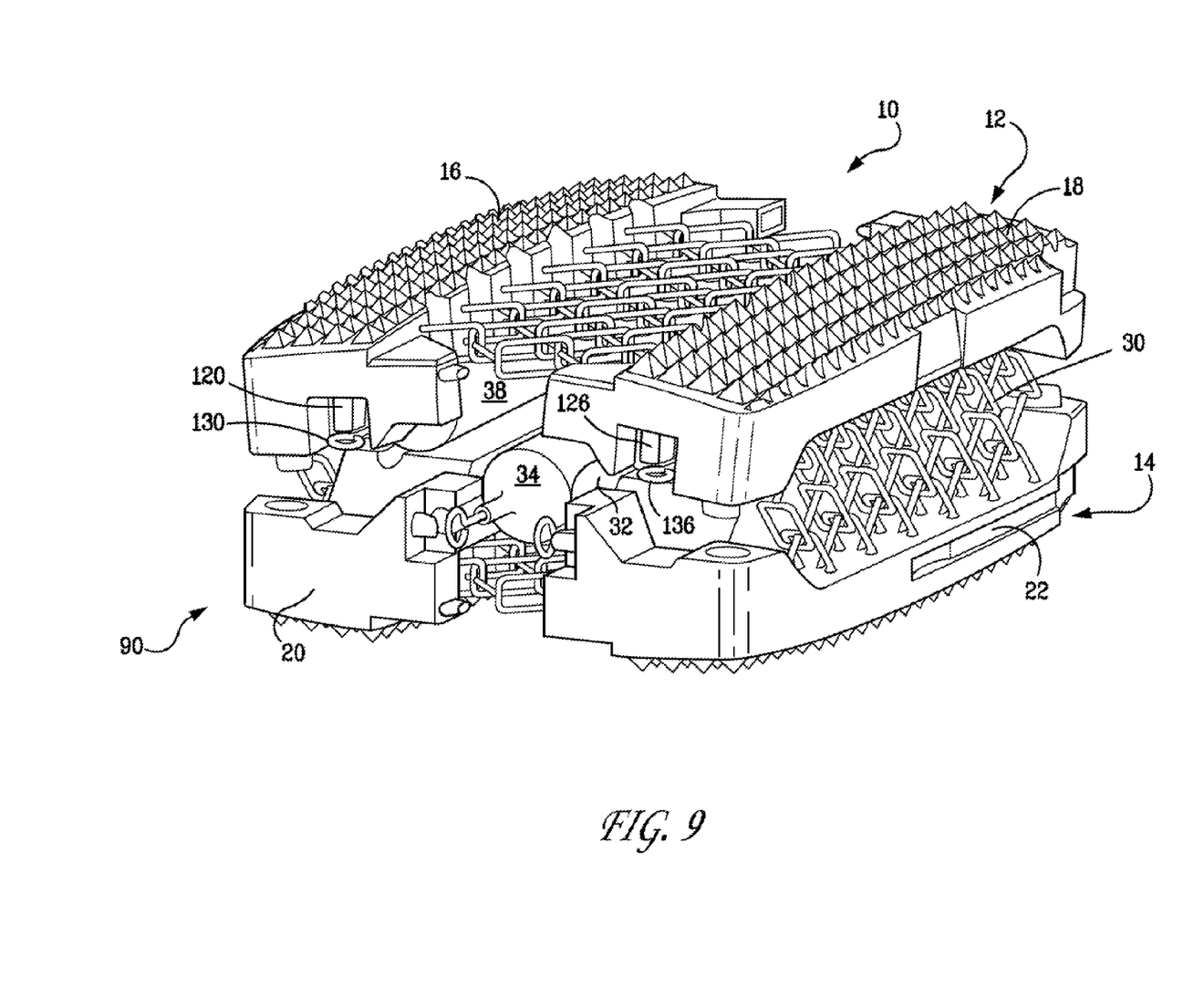
FIG. 9 is a rear perspective view of the implant shown in FIG. 1 which has been expanded in a first direction and in a second direction.

With reference to FIGS. 8 and 9, as the first expansion compartments (32, 34) expand, the contacting components (16, 18) of the first contacting member move apart, the contacting components (20, 22) of the second contacting member move apart and the first and second expandable connections (24, 26) expand. This expansion allows the hook portions (132, 134) of first expansion compartments (32, 34) to slide off the first fixings (122, 124) and hence the first expansion compartments (32, 34) detach from the implant (10).

As the second expansion compartments (36, 38) expand, the contacting components (16, 18) of the first contacting member move apart from the contacting components (20, 22) of the second contacting member and the third expandable connection (30) expands. This expansion allows the hook portions (130, 136) of the second expansion compartments (36, 38) to slide off the second fixings (120, 126) and hence the second expansion compartments (36, 38) detach from the implant (10).

With reference to FIG. 9, following detachment of the first and second expansion compartments (32, 34, 36, 38), the contacting components (16, 18) of the first contacting member (12) are able to tilt relative to each other and relative to the respective contacting components (20, 22) of the second contacting member (14).

Figure 10:
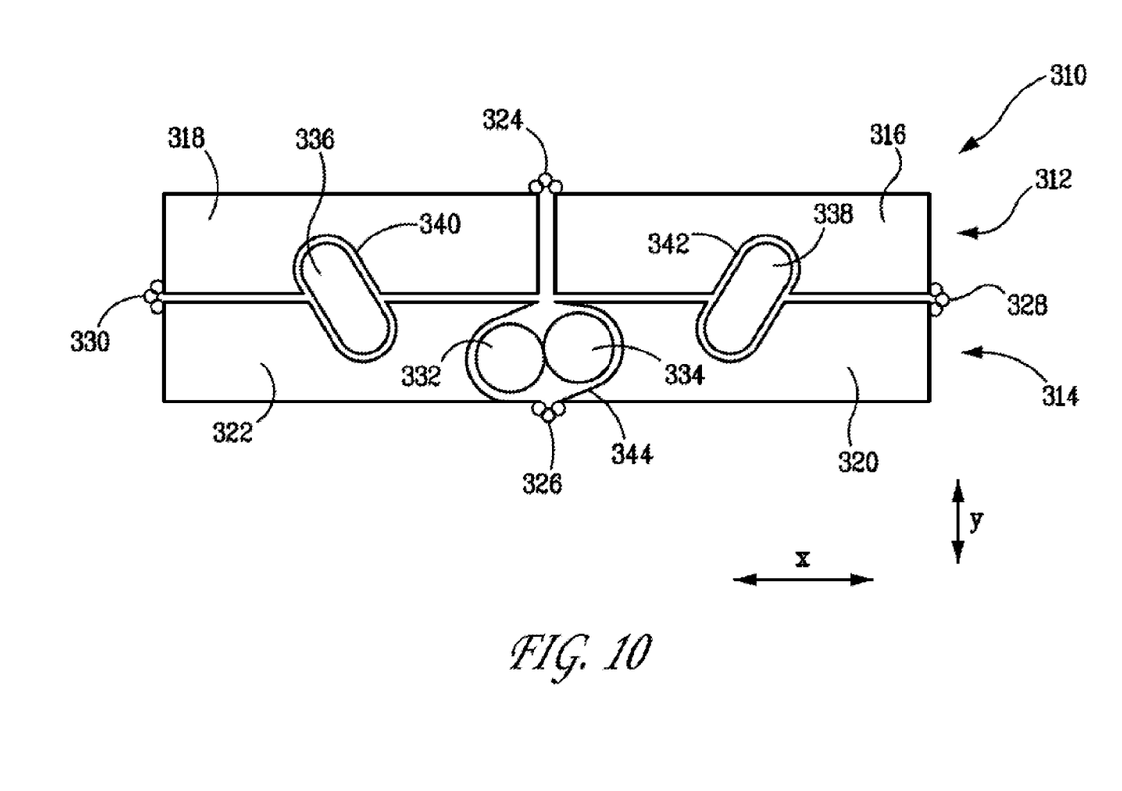
FIG. 10 is a cross-section view of an alternative implant according to the present invention in an insertion configuration.

With reference to FIG. 10, an implant (310) according to an alternative embodiment of the present invention is shown in an insertion configuration. The implant (310) has a first contacting member (312) consisting of two contacting components (316, 318) linked by a first expandable connection (324) and a second contacting member (314) consisting of two contacting components (320, 322) linked by a second expandable connection (326). The first contacting member (312) and the second contacting member (314) are linked by a third expandable connection (328, 330).

The implant (310) has a first cavity (340) between one contacting component (318) of the first contacting member (310) and one contacting component (322) of the second contacting member (314) in which is housed a second expansion compartment (336). The implant (310) also has a second cavity (342) between the other contacting component (316) of the first contacting member (310) and the other contacting component (320) of the second contacting member (314) in which is housed a further second expansion compartment (338).

The implant (310) has a third cavity (344) between the contacting components (320, 322) of the second contacting member (314) in which are housed two first expansion compartments (332, 334).

Expansion of the first expansion compartments (332, 334) causes the contacting components (320, 322) of the second contacting member (314) to move apart and the first and second expandable connections (324, 326) to expand. In this way, the implant (310) increases in dimension in a first direction (x). Due to the angled shape of the cavities (340, 342) between the first and second expansion members (312,314), expansion of the second expansion compartments (336, 338) causes the first contacting member (312) to move apart from the second contacting member (314), causing the third expandable connection (328, 330) to expand and, in addition, causes contacting components (316, 318) of the first contacting member (312) to move further apart and the first expandable connection (324) to further expand.

EXAMPLES

Embodiments of the present invention are now described, by way of illustration only, in the following examples. It will be understood that these examples are not limiting and that variations and modifications may be made within the spirit and scope of the invention as set out above and as defined in the following claims.

Example 1

Four separate catheter balloons (OPN NC® High Pressure PTCA Balloons from Sis Medical, having a highest rated burst pressure of 35 bar) were inserted into a bottom end of a cannulated implant holding and insertion instrument and pushed through the instrument such that part of the tubes connected to the catheter balloons were retained within the instrument but catheter balloons protruded from the top end of the instrument. The four balloons were subsequently inserted into an implant as shown in FIG. 1. The implant was mounted on the implant holding and insertion instrument using a pair of protruding blade springs which engaged with grooves on either side of the implant and retained the implant in a compressed, insertion configuration.

A lateral incision was made in a cadaveric specimen and residual intervertebral disc material was removed between the L3 and L4 vertebrae. The implant was inserted in a compressed, insertion configuration into the L3 to L4 intervertebral disc space.

A first inflation device (High Pressure Inflation Device from Sis Medical) was attached to the two balloons arranged to cause anterior-posterior expansion and a second inflation device of the same type was attached to the two balloons arranged to cause cranio-caudal expansion. The implant holding and insertion instrument was detached from the implant.

Water at a pressure of between 24 and 30 bar was introduced into the two balloons arranged to cause antero-posterior expansion using the first inflation device. The anterior-posterior dimension of the implant increased without causing any increase in the cranio-caudal dimension of the implant.

Subsequently, water at a pressure of between 24 and 30 bar was introduced into the two balloons arranged to cause cranio-caudal expansion using the second inflation device. The cranio-caudal dimension of the implant increased without causing any increase in the anterior-posterior dimension of the implant. A biomechanical study of the resulting expanded implant showed that it stabilized the L3 and L4 vertebrae.

Example 2

Four separate catheter balloons (OPN NC® High Pressure PTCA Balloons from Sis Medical, having a highest rated burst pressure of 35 bar) were inserted into a bottom end of a cannulated implant holding and insertion instrument and pushed through the instrument such that part of the tubes connected to the catheter balloons were retained within the instrument but catheter balloons protruded from the top end of the instrument. The four balloons were subsequently inserted into an implant as shown in FIG. 1. The implant was mounted on the implant holding and insertion instrument using a pair of protruding blade springs which engaged with grooves on either side of the implant and retained the implant in a compressed, insertion configuration.

A lateral incision was made in a cadaveric specimen and residual intervertebral disc material was removed between the L3 and L4 vertebrae. The implant was inserted in a compressed, insertion configuration into the L3 to L4 intervertebral disc space.

A first inflation device (High Pressure Inflation Device from Sis Medical) was attached to the two balloons arranged to cause anterior-posterior expansion and a second inflation device of the same type was attached to the two balloons arranged to cause cranio-caudal expansion. The implant holding and insertion instrument was detached from the implant.

Polymethyl methacrylate (PMMA) cement in a fluid state and at a pressure of between 24 and 30 bar was introduced into the two balloons arranged to cause anterior-posterior expansion using the first inflation device. The anterior-posterior dimension of the implant increased without causing any increase in the cranio-caudal dimension of the implant.

Subsequently, PMMA cement at a pressure of between 24 and 30 bar was introduced into the two balloons arranged to cause cranio-caudal expansion using the second inflation device. The cranio-caudal dimension of the implant increased without causing any increase in the anterior-posterior dimension of the implant.

The PMMA cement was cured. After curing of the PMMA cement, the tubes attached to the balloon catheters were removed. A biomechanical study of the resulting expanded implant showed that it stabilized the L3 and L4 vertebrae.

The invention claimed is:

1. An implant for inserting into an intervertebral space between a superior surface of a first vertebra and an inferior surface of an adjacent, second vertebra, the implant comprising:
    a first contacting member having a bone contacting surface designed to engage the inferior surface of the second vertebra;
    a second contacting member having a bone contacting surface designed to engage the superior surface of the first vertebra;
    at least one first expansion compartment; and
    at least one second expansion compartment;
    wherein the implant is expandable from an insertion configuration to an expanded configuration,
    wherein the implant has a first dimension in a first direction and a second dimension in a second direction in the insertion configuration, and wherein the first direction is substantially perpendicular to the second direction,
    wherein the implant is configured such that:
    during expansion of the at least one first expansion compartment, the at least one first expansion compartment cooperates with at least one of the first and second contacting members to cause the first dimension of the implant to increase without substantially causing a change in the second dimension of the implant; and
    during expansion of the at least one second expansion compartment, the at least one second expansion compartment cooperates with at least one of the first and second contacting members to cause the second dimension of the implant to increase.

2. The implant of claim 1, wherein the implant is configured such that during expansion of the at least one second expansion compartment, the at least one second expansion compartment cooperates with at least one of the first and second contacting members to cause the second dimension of the implant to increase without substantially causing a change in the first dimension of the implant.

3. The implant of claim 2 wherein the first direction is an anterior-posterior (a-p) direction and the second direction is a cranio-caudal (c-c) direction.

4. The implant of claim 1 wherein the first expansion compartment is an inflatable balloon.

5. The implant of claim 4 wherein the second expansion compartment is an inflatable balloon.

6. The implant of claim 5 comprising two or more first expansion compartments.

7. The implant of claim 6 comprising two or more second expansion compartments.

8. The implant of claim 1 wherein the first contacting member comprises a first and a second contacting component and a first expandable connection that links the first and second contacting components, and
    wherein the first and second contacting components of the first contacting member are arranged such that as the first dimension of the implant increases the first expandable connection expands and the contacting components move apart relative to each other.

9. An implant for inserting into an intervertebral space between a superior surface of a first vertebra and an inferior surface of an adjacent, second vertebra, and having an insertion, distal end and an opposite trailing, proximal end, the implant comprising:
    a first contacting member having a bone contacting surface designed to engage the inferior surface of the second vertebra, the first contacting member being separated into a first and a second contacting component having a first expandable connection that links the first contacting component with the second contacting component;
    a second contacting member having a bone contacting surface designed to engage the superior surface of the first vertebra, the second contacting member being separated into a third and a fourth contacting component having a second expandable connection that links the third contacting component with the fourth contacting component;
    a third expandable connection that links the first contacting member with the second contacting member;
    a first elongated expansion balloon having a length substantially greater than an un-inflated diameter, and extending lengthwise in the direction of the proximal to the distal end of the implant; and
    a second elongated expansion balloon having a length substantially greater than an un-inflated diameter, and extending lengthwise in the direction of the proximal to the distal end of the implant;
    wherein the implant is expandable from an insertion configuration to an expanded configuration,
    wherein the implant has an initial width in a first direction and an initial height in a second direction in the insertion configuration, and wherein the first direction is substantially perpendicular to the second direction,
    wherein the implant is configured such that:
    during expansion of the first balloon, the balloon forces the first and second contacting components apart and the third and fourth contacting components apart to cause the width of the implant to increase without substantially causing a change in the height of the implant; and
    during expansion of the second balloon, the balloon forces the first contacting member apart from the second contacting member to cause the height of the implant to increase.

10. The implant of claim 9 wherein the implant contains a third elongated expandable balloon parallel to the first balloon.

11. The implant of claim 10 wherein the implant contains a fourth elongated expandable balloon parallel to the second balloon.

12. The implant of claim 9 wherein the first expandable connection comprises wire netting.

13. The implant of claim 12 wherein the wire netting comprises a plurality of individual link members.

14. A method for using an expandable intervertebral implant having a first contacting member having a first bone contacting surface, a second contacting member having a second bone contacting surface, and at least one expandable connection that links the first contacting member to the second contacting member, the intervertebral implant configured to be positioned into an intervertebral space between a superior surface of a first vertebra and an inferior surface of an adjacent, second vertebra such that the first bone contacting surface faces the inferior surface of the second vertebra and the second bone contacting surface faces the superior surface of the first vertebra, the method comprising the steps of:
    inserting the expandable implant in the intervertebral space, the implant comprising first and second expansion compartments;
    expanding the first expansion compartment to move each of the first and second contacting members in a first direction, thereby expanding a first dimension of the implant; and subsequently expanding the second expansion compartment to move the first and second contacting members apart in a second direction, thereby 1) expanding a second dimension of the implant, and 2) expanding the at least one expandable connection;

wherein the first direction is different than the second direction, and the first expanding step is performed without substantially causing a change in the second dimension of the implant.

15. The method of claim 14, further comprising positioning the first and second expansion compartments in the expandable implant prior to the step of inserting the expandable implant into the intervertebral space.

16. The method of claim 14 wherein there is substantially no expansion of the first dimension of the implant in the first direction during the step of subsequently expanding the second expansion compartment.

17. The method of claim 14 wherein the first direction is substantially perpendicular to the second direction.

18. The method of claim 16 wherein there is substantially no expansion of the first dimension of the implant in a first direction during the step of expanding the second expansion compartment.

19. The method of claim 18 wherein the first dimension of the implant is the width of the implant and the second dimension of the implant is the height of the implant.

20. The method of claim 19 wherein the expanding steps for both dimensions comprises injecting fluid into an inflatable balloon.

21. The method of claim 14, wherein each of the first and second contacting members comprises respective first and second contacting components and an expandable connection that links each of the first and second contacting components to each other, and the first expanding step comprises moving the first and second contacting components apart relative to each other so as to expand the respective expandable connections.

22. The method of claim 14, wherein 1) the implant further comprises at least one first expansion compartment and at least one second expansion compartment separate from the at least one first expansion compartment, such that the second expansion compartment does not contact the first expansion compartment, 2) the first expanding step comprises expanding the at least one first expansion compartment so as to move each of the first and second contacting members in the first direction, and 3) the subsequently expanding step comprises expanding the at least one second expansion compartment so as to move the first and second contacting members apart in the second direction.

* * * * *